United States Patent
Kossak et al.

(10) Patent No.: US 6,494,778 B2
(45) Date of Patent: Dec. 17, 2002

(54) AROMA DISPENSING UNIT IN A HVAC SYSTEM OF AN AUTOMOBILE

(75) Inventors: Irene Olha Kossak, Dearborn, MI (US); Timothy James Hall, Novi, MI (US); John David Hoeschele, Canton, MI (US)

(73) Assignee: Visteon Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/740,312

(22) Filed: Dec. 18, 2000

(65) Prior Publication Data

US 2002/0077058 A1 Jun. 20, 2002

(51) Int. Cl.$^7$ ................................................. B60H 3/02
(52) U.S. Cl. ...................... 454/157; 454/328; 422/124; 222/416
(58) Field of Search ................................ 454/110, 157, 454/337, 328; 422/123, 124; 222/152, 204, 416

(56) References Cited

U.S. PATENT DOCUMENTS

| | | | |
|---|---|---|---|
| 33,565 A | * 10/1861 | Beardsley | .................... 261/106 |
| 82,810 A | * 10/1868 | Dripps | ......................... 237/30 |
| 282,889 A | * 8/1883 | Hill | ......................... 261/119.1 |
| 3,259,050 A | 7/1966 | Grimm, III | |
| 5,019,352 A | 5/1991 | Gonzalez | |
| 5,071,621 A | 12/1991 | Tokuhiro et al. | |
| 5,102,189 A | 4/1992 | Saito et al. | |
| 5,297,988 A | 3/1994 | Nishino et al. | |
| 5,311,616 A | 5/1994 | Pratt | |
| 5,370,274 A | 12/1994 | Ohmi et al. | |
| 5,429,180 A | 7/1995 | Nishino et al. | |
| 5,529,536 A | 6/1996 | Sizemore et al. | |
| 5,664,423 A | 9/1997 | Akazawa | |
| 5,694,989 A | 12/1997 | Kupelian | |
| 6,012,649 A | 1/2000 | Riddell et al. | |

* cited by examiner

*Primary Examiner*—Derek Boles
(74) *Attorney, Agent, or Firm*—Brinks Hofer Gilson & Lione

(57) ABSTRACT

The present invention provides for an aroma-dispersing unit in the HVAC system of an automobile. The aroma-dispersing unit includes a passageway and an aroma cartridge housed in an aroma cartridge housing. The passageway includes a first portion, a low-pressure zone and a second portion. The low-pressure zone defines an opening. The aroma cartridge is in communication with the low-pressure zone. The aroma cartridge also defines an opening at the top of the aroma cartridge. The opening of the low-pressure zone and the opening of the aroma cartridge are alignable such that air passing through the low-pressure zone can extract aroma from the aroma cartridge. The aroma mixed air enters the second portion of the passageway where it is dispersed into the interior of the automobile. The amount of aroma extracted from the aroma cartridge can be varied by adjusting the proximity of the opening of the aroma cartridge relative to the opening of the low-pressure zone.

28 Claims, 4 Drawing Sheets

AROMA DISPENSING UNIT IN A HVAC SYSTEM OF AN AUTOMOBILE

BRIEF SUMMARY OF THE INVENTION

This patent discloses and claims a useful, novel, and unobvious invention for an aroma-dispensing unit in the HVAC system of an automobile.

DETAILED DESCRIPTION OF THE PREFERRED EMBODIMENTS

The following description of the preferred embodiment is merely exemplary in nature, and is in no way intended to limit the invention or its application or uses.

Figure 1:
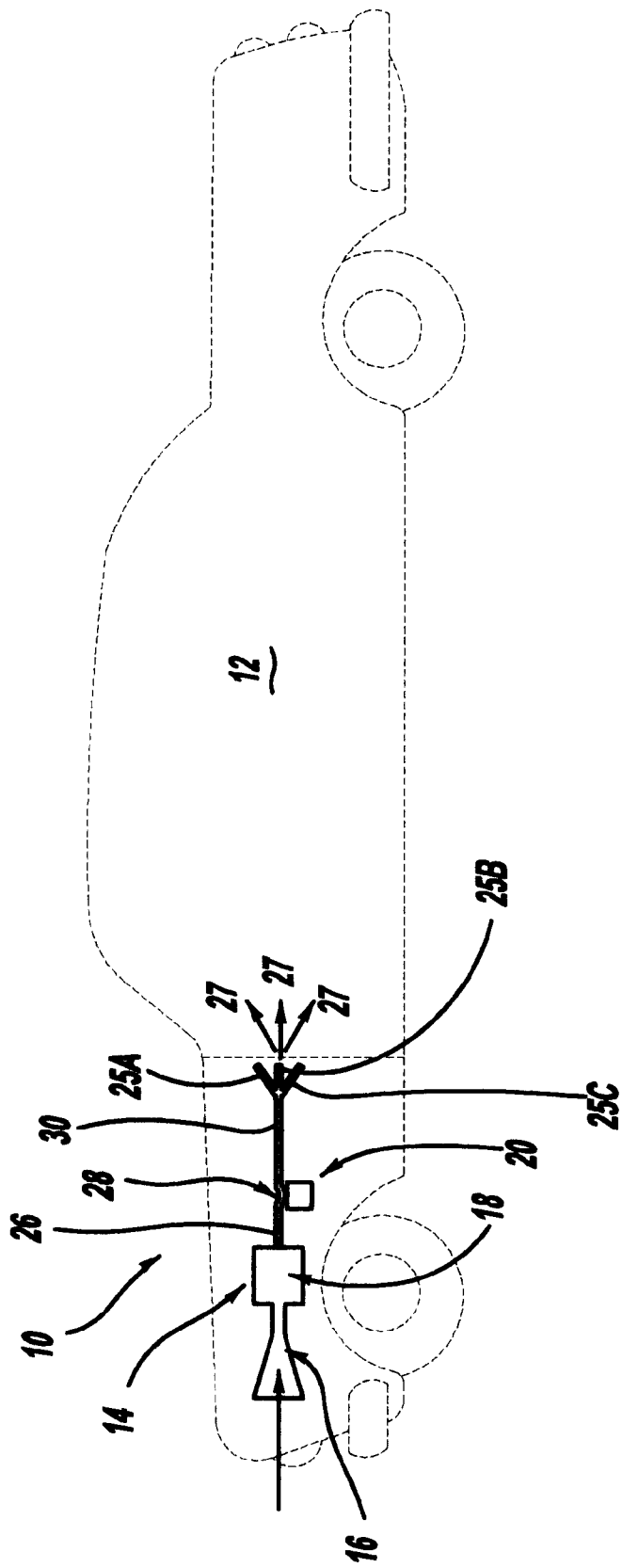
FIG. 1 is a partial view of the automobile including the features of the HVAC system of the preferred embodiment invention.

A representative automobile incorporating the features of the present invention is shown in FIG. 1 and generally designated by reference number 10. The automobile 10 defines an interior compartment 12 and a heat ventilation air conditioning (HVAC) system 14. The HVAC system is generally installed in the vicinity of an engine (not shown) in the automobile 10. The HVAC system, which functions to heat and cool the interior 12 of the automobile 10, comprises a blower unit 16, a heat transfer unit 18 and an aroma-dispersing unit 20.

The blower unit 16, which is well known in the automotive industry, preferably includes a motor, a fan, and plurality of sensors (not shown in the Figure). The blower unit 16 may alternatively not include some of these elements or may alternatively include other elements to supply a stream of air to the HVAC system 14 when activated. The heat transfer unit 18, which functions to either transfer heat to the air or remove heat from the air supplied by the blower unit 16, preferably includes a heating device, air conditioning device, and an air filter device (not shown in Figures), but may alternatively include other suitable devices. Like the blower unit 16, the heat transfer unit 18 is also well known in the art.

Figure 2:
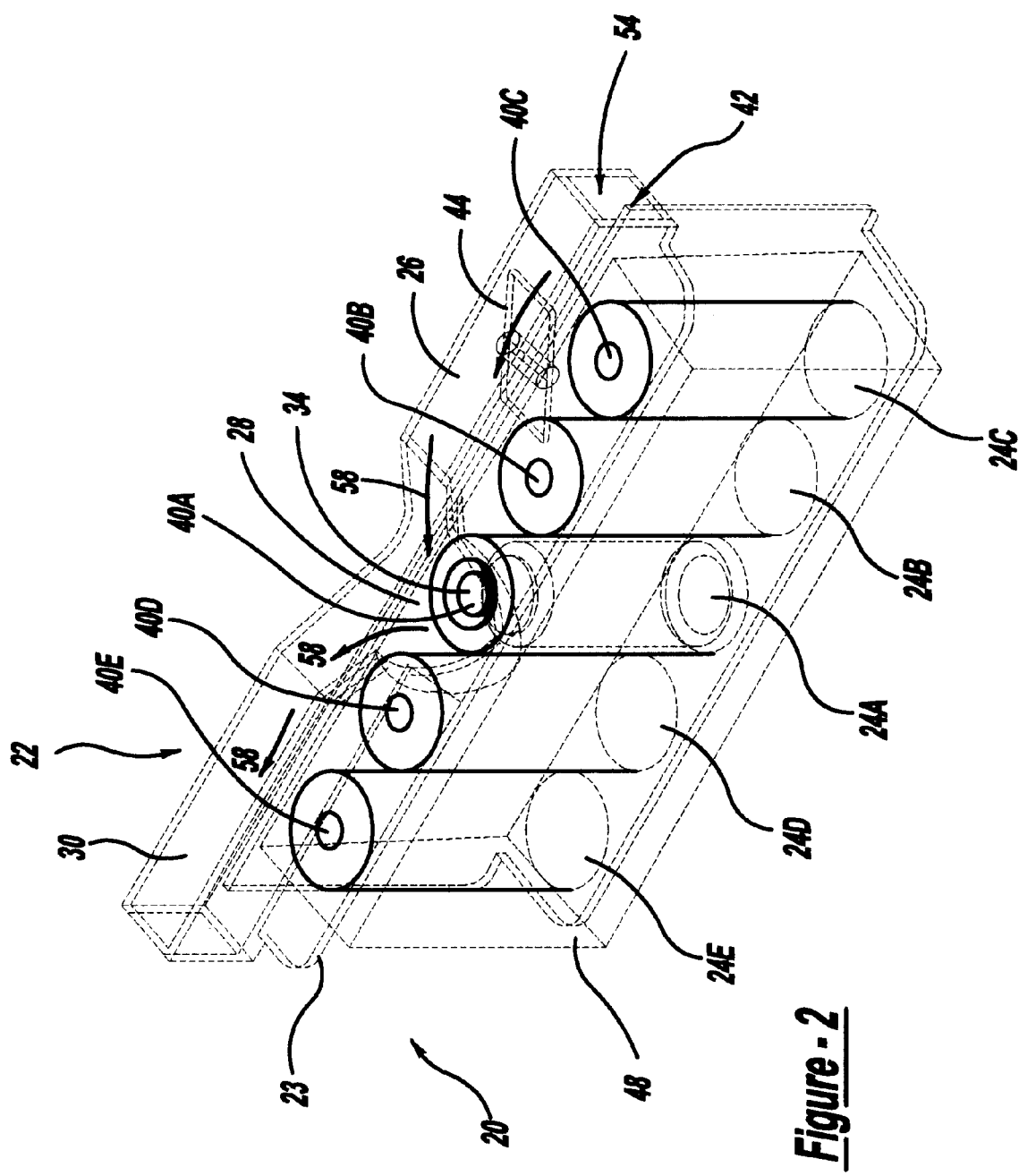
FIG. 2 is a perspective view of the aroma-dispersing unit of the preferred embodiment of the invention.

As shown in FIG. 2, the aroma-dispersing unit 20 preferably includes a passageway 22 and an aroma cartridge 24 preferably disposed in the interior of an aroma cartridge housing 23. The passageway 22 preferably functions to allow the air to pass from the heat transfer unit 18 to the interior 12 of the automobile 10, but may alternatively function to allow the air to pass from any portion of the HVAC system 10 to the next. The passageway 22 preferably includes a first portion 26, a low-pressure zone 28 and a second portion 30.

The first portion 26 of the passageway 22 is preferably connected to the heat transfer unit 18 and functions to receive air from the heat transfer unit 18. Alternatively, the first portion 26 may also be directly connected to the blower unit 16 or any other device from which the first portion 26 can receive air. The first portion 26 preferably has a tubular cross section and a hollow interior, however it is possible to configure the first portion in any suitable manner to allow air to travel through it.

Figure 3:
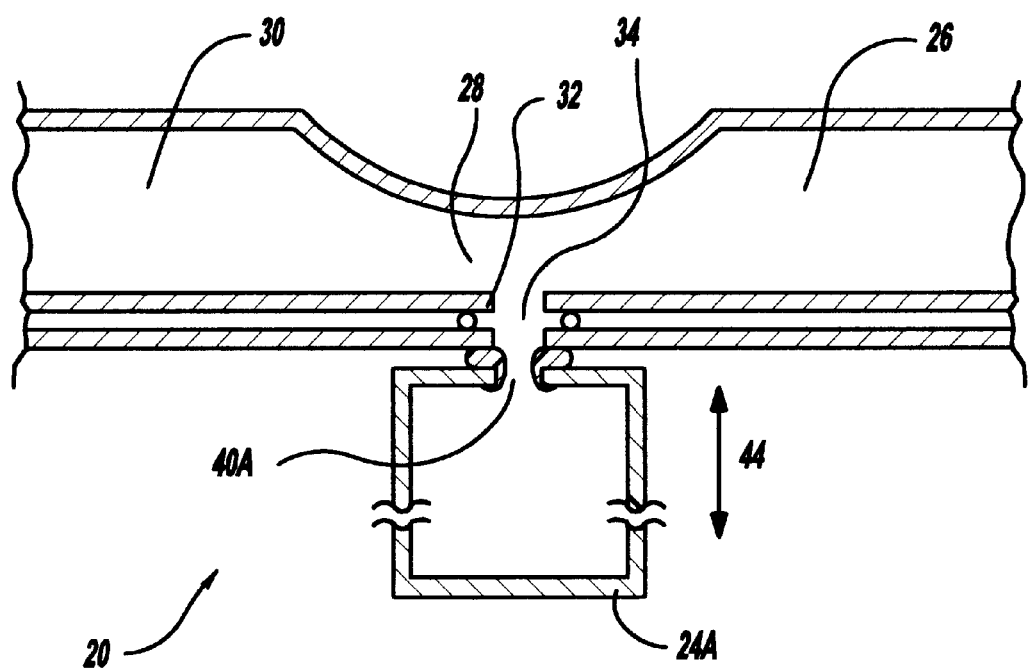
FIG. 3 is a partial cross-sectional view of the aroma-dispersing unit of the preferred embodiment of the invention.

The low-pressure zone 28 of the passageway 22 is preferably connected at one end to the first portion 26 and at the other end to the second portion 30. The low-pressure zone 28 functions to reduce the pressure of the air passing through it such that an aroma is extracted from an aroma cartridge 24. As shown in FIG. 3, the reduced cross-section of the passageway 22 acts as a conventional venturi to create the low-pressure zone 28. Preferably, the venturi is configured like a funnel such that it will accelerate the air passing through the funnel. The base 32 of the low-pressure zone 28 defines an opening 34. As will be explained later, the opening 34 in the low-pressure zone 28 will facilitate the extraction of an aroma from an aroma cartridge 24.

As shown in FIG. 2, the second portion 30 of the passageway is connected to the low-pressure zone 28 and functions to disperse air from the low-pressure zone 28 to the interior 12 of vehicle. The second portion 30 is preferably connected, either directly or indirectly, at one end to multiple vent ducts 25A, B, and C such that vents face the interior 12 of the automobile 10 (as shown in FIG. 1).

As shown in FIG. 1, the air is preferably dispersed in the interior 12 of the automobile 12 (as shown by the arrows 27). The second portion 30 preferably has the same cross section and dimension as the first portion 26. Therefore, like the first portion 26, the second portion 30 preferably has a tubular cross section and hollow interior.

The first portion 26, the low-pressure zone 28 and the second portion 30, are preferably configured as one integral piece and lie in a linear plane. Alternatively, it is possible to have the first portion 26, the low-pressure zone 28 and the second portion 30 as modular separate pieces or in different planes.

Figure 4:
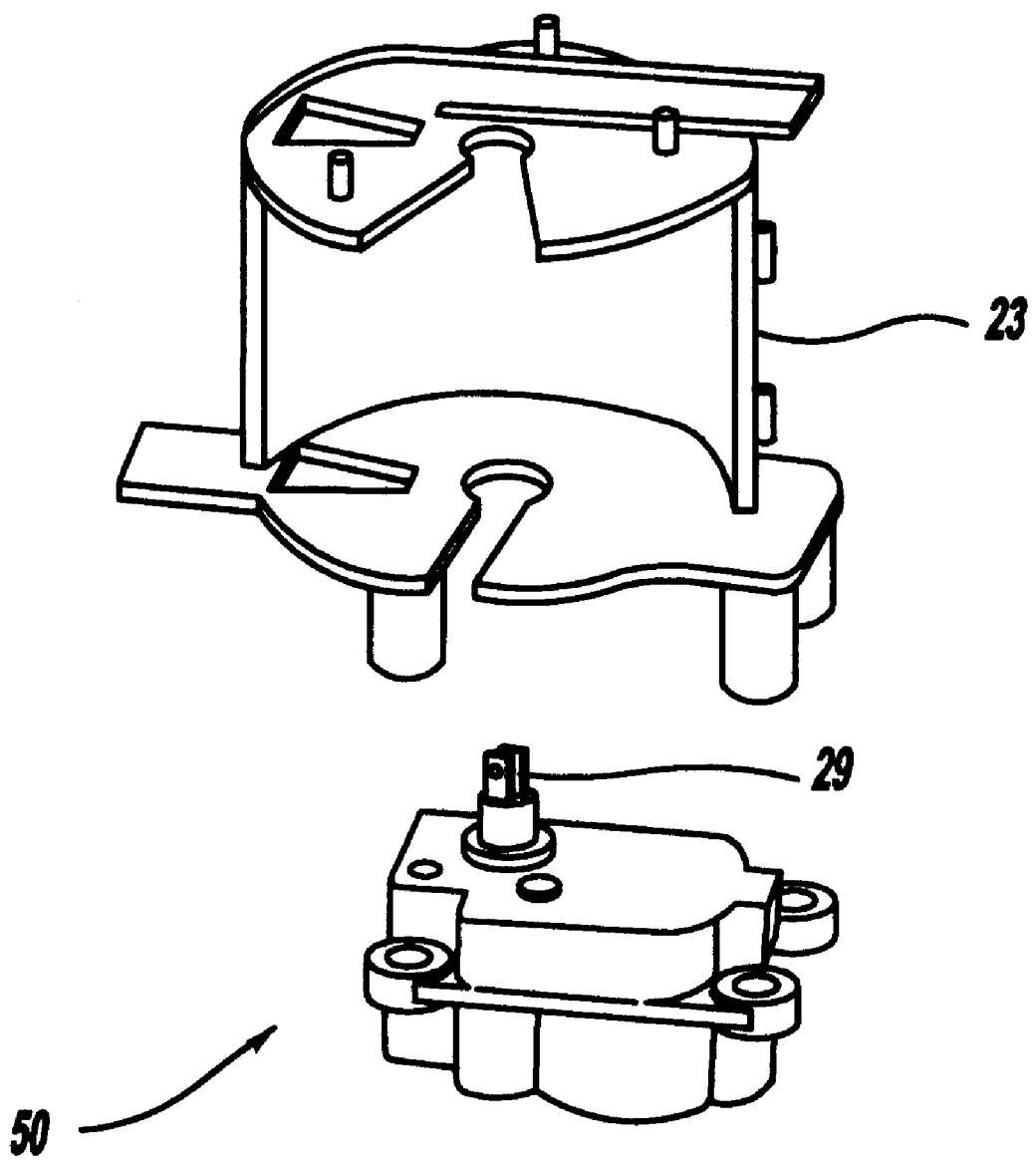
FIG. 4 is a perspective view of an aroma cartridge having a circular configuration and a rotational actuator of a second preferred embodiment of the invention.

As shown in FIG. 2, the aroma-dispersing unit 20, in addition to the passageway 22, preferably includes multiple aroma cartridges 24 A–E disposed in the interior of an aroma cartridge housing 23. The aroma cartridge housing 23 is preferably linearly configured such that the aroma cartridges 24 A–E are linearly aligned in the interior of the housing. Alternatively, it is also possible to have the aroma cartridges housing 23 has a substantially circular configuration such that the housing 23 is capable of rotating around a central axis 29 (as shown in FIG. 4). The aroma cartridge housing 23 may include a cover to protect the aroma cartridges 24 A–E.

The aroma cartridges 24 A–E function to hold aromas desired by the operator of the automobile 10. Although it is preferred that different aroma cartridges hold different aromas, it is possible that two or more aroma cartridges have the same aroma. In this alternative manner, the operators of the automobile are less likely to run out of their favorite aroma. The aroma cartridges 24 A–E are generally solid and are generally air impermeable. Each aroma cartridges 24 A–E are preferably easily replaceable by removing the cover of the aroma cartridges housing 23 and substituting old aroma cartridges with new ones.

The aroma cartridges 24 A–E preferably have corresponding openings 40A–E. An aroma is extracted from the aroma cartridges 24 A–E by aligning the openings 40 A–E with the opening 34 of the low-pressure zone 28 along the axis 42 such that at least one of the openings 40 A–E is in contact with the opening 34. In this position, where at least one of the aroma cartridges 24 is in communication with the opening 34 of the low-pressure zone 28, the air passing through the low-pressure zone extracts the maximum amount of aroma from the aroma cartridges.

The aroma-dispersing unit 20 preferably includes means for controlling the amount of aroma extracted from the aroma cartridges 24 A–E by the air passing through the low-pressure zone 28. Preferably, the means is an proximity actuator having a motor and a gear among other elements. The proximity actuator helps to shift the aroma cartridge closer and further along the directions 44 (as shown in FIG. 3). When the aroma cartridge shifts in the direction as discussed above, the opening 34 of the low-pressure zone is no longer in contact with one of the openings of the aroma cartridge. Hence, the amount of aroma extracted by the air passing the low-pressure zone 34 is reduced as compared to the amount of aroma extracted when the opening of the low-pressure zone 34 is in contact with the opening of the aroma cartridge 24 A–E (shown in FIG. 3).

As shown in FIG. 2, the aroma-dispersing unit 20 also preferably includes means for displacing the aroma cartridges 24 A–E relative to the low-pressure zone such that the opening 34 of the low-pressure zone 28 is out of alignment with the opening 40A of the aroma cartridge 24A to substantially reduce the amount of aroma extracted by air passing through the low-pressure zone 28. The means for displacing the aroma cartridges is preferably a linear sleeve 48 that moves relative to the housing 23 such that it linearly displaces the aroma cartridges 24A relative to the opening 34 of the low-pressure zone 28. The linear sleeve 48 also preferably moves the aroma cartridges relative to each other such that air passing through the low-pressure zone 28 can extract aroma from a different aroma cartridge. For example, if it is desired that the aroma be extracted from the aroma cartridge 24B, then the linear sleeve 48 would move the aroma cartridge 24B such that aroma cartridge 24B is now in communication with low-pressure zone 28. Further, it is also preferable that the opening 40B of the aroma cartridge 24B is in contact with the opening 34 of the low-pressure zone 28. The linear sleeve 48 preferably includes a linear actuator with a gear and a motor to substantially displace the aroma cartridges, but may alternatively include other suitable devices.

Alternatively, if the aroma cartridge housing 23 has a circular configuration as opposed to a linear configuration as discussed above, the means for displacing the aroma cartridges relative to one other or with respect to the opening 34 in the low-pressure zone 28 may include a rotational sleeve 50 (as shown in FIG. 4). Like the linear sleeve, the rotational sleeve preferably includes a rotational actuator with a motor and a set of gears to help perform the necessary function, but may alternatively include other suitable devices.

As shown in FIG. 2, the present invention preferably provides for more than one aroma to be extracted simultaneously from different aroma cartridges. This is preferably attained by moving the aroma cartridges with the help of a linear sleeve or an rotational sleeve such that a portion 52 of the opening 40A and 40B of two different aroma cartridges 24A and 24B are in alignment with the opening 34 of the low-pressure zone 28. When the aroma cartridges 24A and 24B are positioned in the above-described manner the air passing through the low-pressure zone 28 extracts the aroma from both aroma cartridges. Therefore, the aroma-mixed air dispersed in the interior of the automobile has more than one aroma.

In addition to the blower unit 16, a heat transfer unit 18 and an aroma-dispersing unit 20, the HVAC system 14 may include locking means 46 (as shown in FIG. 2) to shut off the air supply to the aroma-dispersing unit 20 and prevent the air from passing through the low-pressure zone 28. The locking means 46 is preferably positioned between the heat transfer unit 18 and the first portion 26 of the passageway 22. The locking means 46 is preferably configured in the form of a valve, or alternatively in the form of a locking door. Alternatively, the locking means 46 may be configured to be a part of the aroma-dispersing unit 20. The locking means 46 may be positioned in the first portion 26 or the second portion 28 of the passageway 22.

As shown in FIG. 2, the aroma is dispersed in the interior 12 of the automobile 10 in the following manner. When the HVAC system 14 is activated, the blower unit 16 blows air through the HVAC system 14. The air (as shown by arrows) preferably enters the heat transfer unit 18 such that heat is either taken from or supplied to the air. The air from the heat transfer unit 18 then enters the first portion 26 of the passageway 22, as indicated by arrow 54 (in FIG. 2). The air then passes through the low-pressure zone 28, as indicated by arrows 56, where the aroma present in the aroma cartridge 24A is extracted. The aroma-filled air, as indicated by arrow 58, then passes through the second portion 30 such it is dispersed in the interior 12 of the automobile 10 through a plurality of ducts 25A, B, and C (as shown in FIG. 1).

As any person skilled in the art of HVAC system will recognize from the previous description and from the figures and claims, modifications and changes can be made to the preferred embodiment of the invention without departing from the scope of the invention.

What is claimed is:

1. A Heat Ventilation Air Conditioning (HVAC) system for dispersing an aroma into the interior of an automobile, said system comprising:

a blower unit to blow air into the HVAC system;

a heat transfer unit to transfer heat to and from the air;

an aroma-dispersing unit including a passageway and a plurality of aroma cartridges;

wherein the passageway having a first portion, a second portion and a low-pressure zone between the first portion and the second portion, wherein the low-pressure zone defines a first opening, and wherein the air enters the passageway through the first portion, passes through the low-pressure zone and exits the passageway through the second portion; and wherein the plurality of aroma cartridges defines a plurality of second openings selectively alignable with the first opening of the low-pressure zone.

2. The system of claim 1 wherein each of the plurality of aroma cartridges defines one of the plurality of second openings.

3. The system of claim 2 further including means for selectively adjusting the proximity of the plurality of second openings of the plurality of aroma cartridges relative to the first opening of the low-pressure zone to vary the amount of aroma extracted by air passing through the low-pressure zone.

4. The system of claim 1 wherein the first portion receives air from the heat transfer unit.

5. The system of claim 1 wherein the second portion includes a plurality of vent ducts such that aroma extracted from air passing the low-pressure zone passes through the second portion and is dispersed into the interior of the automobile through the plurality of vent ducts.

6. The system of claim 1 further including means for displacing the plurality of aroma cartridges relative to the low-pressure zone such that the first opening of the low-pressure zone is out of alignment with one of the plurality of second openings to substantially reduce the amount of aroma extracted by air passing through the low-pressure zone.

7. The system of claim 6 wherein the means include a linear actuator.

8. The system of claim 6 wherein the means include a rotational actuator.

9. The system of claim 1 wherein the aroma in the plurality of aroma cartridges is identical.

10. The system of claim 1 wherein the aroma in at least one of the plurality of aroma cartridges is different.

11. The system of claim 1 wherein selected portions of the plurality of second openings are in alignment with the first opening of the low-pressure zone such that aroma is simultaneously extracted from more than one of the plurality of aroma cartridges.

12. The system of claim 1 wherein each of the plurality of aroma cartridges is generally solid.

13. The system of claim 1 wherein each of the plurality of aroma cartridges is generally impermeable.

14. The system of claim 1 further including means for preventing air from passing through the low-pressure zone.

15. An aroma-dispersing unit in HVAC system for dispersing an aroma into the interior of a automobile comprising:
   a passageway having a first portion, a second portion and a low-pressure zone between the first and the second portion, wherein the low-pressure zone defines a first opening, and wherein the air enters the passageway through the first portion and passes through the low-pressure zone and exits the passageway through the second portion; and
   a plurality of aroma cartridges in selective communication with the low-pressure zone, wherein each of the plurality of aroma cartridges defines a second opening alignable with the first opening of the low-pressure zone, such that air passing the low-pressure zone extracts an aroma from at least one of the plurality of aroma cartridges.

16. The aroma-dispersing unit of claim 15 wherein each of the plurality of aroma cartridges defines one of the plurality of second openings.

17. The aroma-dispersing unit of claim 16 further including means for selectively adjusting the proximity of each of the plurality of second openings relative to the first opening of the low-pressure zone to vary the amount of aroma extracted by air passing through the low-pressure zone.

18. The aroma-dispersing unit of claim 15 wherein the first portion receives air from a heat transfer unit in the HVAC system.

19. The aroma-dispersing unit of claim 15 wherein the second portion includes a plurality of vent ducts such that aroma extracted from air passing the low-pressure zone passes through the second portion and is dispersed into the interior of the automobile through the plurality of the vent ducts.

20. The aroma-dispersing unit of claim 15 further including means for displacing the plurality of aroma cartridges relative to the low-pressure zone to substantially reduce the amount of aroma extracted by air passing through the low-pressure zone.

21. The aroma-dispersing unit of claim 20 wherein the means include a linear actuator.

22. The aroma-dispersing unit of claim 20 wherein the means include a rotational actuator.

23. The aroma-dispersing unit of claim 15 wherein the aroma in the plurality of aroma cartridges is identical.

24. The aroma-dispersing unit of claim 15 wherein the aroma in at least one of the plurality of aroma cartridges is different.

25. The aroma-dispersing unit of claim 15 wherein selected portions of the plurality of second openings are in alignment with the first opening of the low-pressure zone such that aroma is simultaneously extracted from more than one of the plurality of aroma cartridges.

26. The aroma-dispersing unit of claim 15 wherein each of the plurality of aroma cartridges is generally solid.

27. The aroma-dispersing unit of claim 15 wherein each of the plurality of aroma cartridges is generally impermeable.

28. The aroma-dispersing unit of claim 15 further including means for preventing air from passing through the low-pressure zone.

* * * * *